United States Patent [19]

Tedder

[11] Patent Number: 4,510,242

[45] Date of Patent: Apr. 9, 1985

[54] PROCESS FOR PRODUCING FUEL GRADE ALCOHOL BY SOLVENT EXTRACTION AND CARRIER GAS STRIPPING

[75] Inventor: Daniel W. Tedder, Marietta, Ga.

[73] Assignee: Georgia Tech Research Corporation, Atlanta, Ga.

[21] Appl. No.: 544,813

[22] Filed: Oct. 24, 1983

Related U.S. Application Data

[63] Continuation of Ser. No. 283,739, Jul. 15, 1981, abandoned.

[51] Int. Cl.$^3$ .............. C12P 7/04; C12P 7/06; C07C 29/86; B01D 1/14
[52] U.S. Cl. .................. 435/157; 435/161; 435/813; 568/916; 568/918; 203/49; 203/19; 203/DIG. 13
[58] Field of Search .............. 435/161, 157, 813; 203/19, 49, DIG. 13; 210/634, 771; 568/918, 916

[56] References Cited

U.S. PATENT DOCUMENTS

| | | | |
|---|---|---|---|
| 1,833,717 | 11/1931 | Laird | 203/19 |
| 2,038,357 | 4/1936 | Hale | 203/19 |
| 2,173,692 | 9/1939 | Marples | 203/19 |
| 2,440,925 | 5/1948 | Boeckeler | 435/162 |
| 2,591,671 | 4/1952 | Catterall | 203/19 |
| 4,143,066 | 3/1979 | Kalcevic | 203/43 |
| 4,306,884 | 12/1981 | Roth | 203/DIG. 13 |
| 4,327,184 | 4/1982 | Johnson et al. | 435/161 |
| 4,345,973 | 8/1982 | Ladisch et al. | 203/19 |
| 4,346,241 | 8/1982 | Feldman | 568/916 |
| 4,399,000 | 8/1983 | Tedder | 203/19 |
| 4,400,241 | 8/1983 | Braithwaite et al. | 568/916 |
| 4,409,406 | 10/1983 | Feldman | 568/916 |

FOREIGN PATENT DOCUMENTS 0497298 10/1953 Canada ................ 435/161

*Primary Examiner*—Raymond Jones
*Assistant Examiner*—Elizabeth C. Weimar
*Attorney, Agent, or Firm*—Newton, Hopkins & Ormsby

[57] ABSTRACT

Alcohol substantially free of water is prepared by fermenting a fermentable biomass feedstock in a fermentation unit, thereby forming an aqueous fermentation liquor containing alcohol; extracting said aqueous fermentation liquor with an organic solvent containing an extractant for said alcohol, thereby forming an alcohol-organic solvent extract phase and an aqueous raffinate; contacting said alcohol-organic solvent phase with a carrier gas thereby separating said alcohol from said alcohol-organic solvent phase and forming an alcohol laden solvent vapor; and separating alcohol substantially free of water from said carrier gas.

11 Claims, 1 Drawing Figure

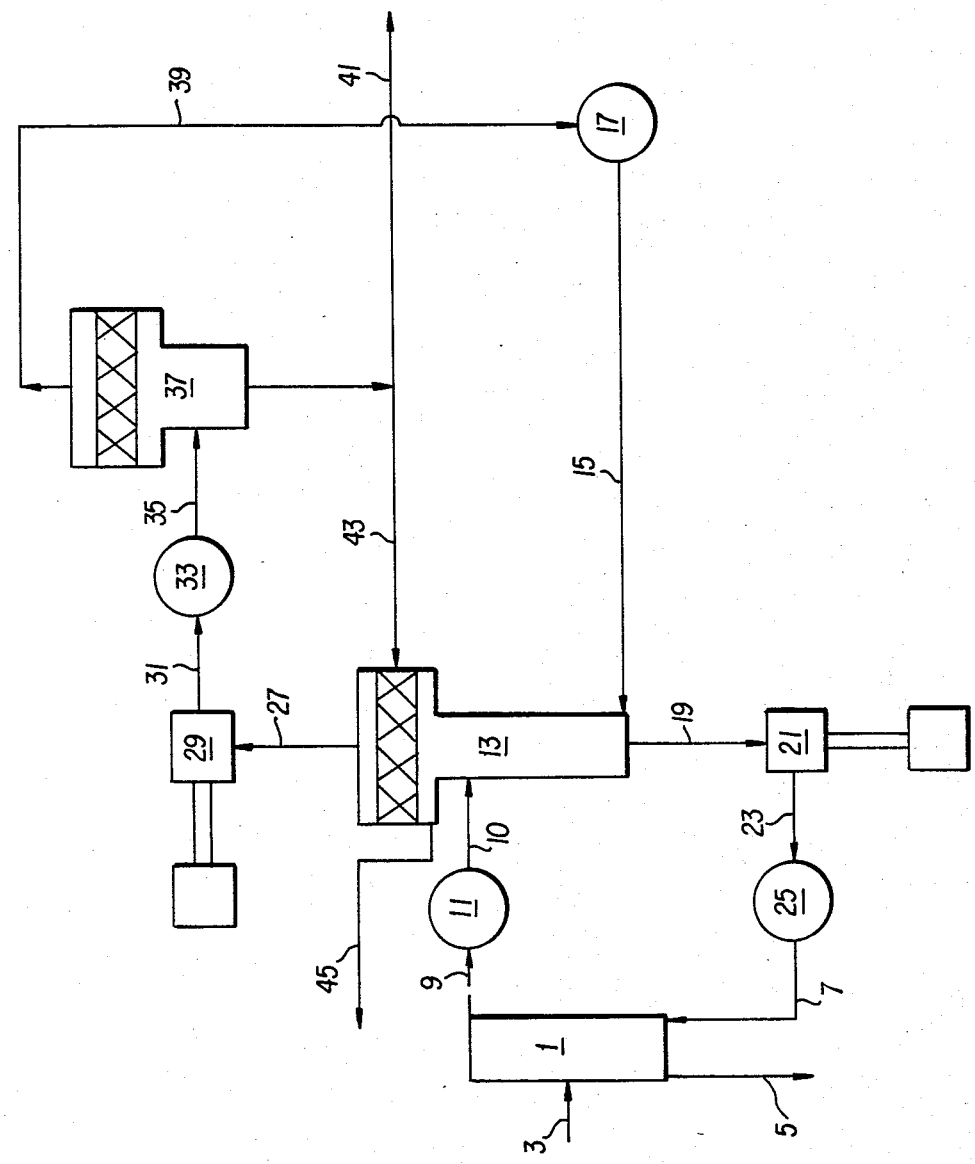

PROCESS FOR PRODUCING FUEL GRADE ALCOHOL BY SOLVENT EXTRACTION AND CARRIER GAS STRIPPING

This application is a continuation of application Ser. No. 283,739 filed July 15, 1981, now abandoned.

BACKGROUND OF THE INVENTION

1. Field of the Invention

The present invention relates to a method for preparing fuel-grade alcohol.

2. Description of the Prior Art

Ethanol as well as other alcohols is commonly prepared by fermentation of sugars or other biological feedstocks. In the fermentation process, the fermentable materials incuding yeast microorganisms are added to a large tank where fermentation is accomplished in a batch process. During fermentation the yeast cells or other microbes used consume the biomass feedstock in the tank and convert the feedstock to alcohol as they grow. The initial rate of fermentation is low, but then increases to a maximum rate which decreases again as the alcohol content in the fermentation medium increases. In fact, in the case of wine production, the relatively high alcohol content in the final product may be sufficient to actually kill the fermenting microorganisms.

After the fermentation has reached the desired stage of completion, the fermentation liquors are drained from the tank. Thereafter, if fuel-grade ethanol is to be recovered from the ferment, the fermentation liquors are clarified in a beer still and then fractionated to produce an ethanol-water azeotrope.

The conventional process for producing absolute ethanol has several drawbacks. One of the disadvantages is that the fermentation step is operated batchwise, which means that the average rate of conversion of fermentable material is lower than would be the case if the fermentation were conducted continuously. Consequently, the quantities of fermentable feedstocks must be maintained at high levels at the processing plant in order to maintain the desired production rate. Secondly, the distillation process for the recovery of ethanol is highly energy intensive. An analysis of the conventional alcohol distillation process shows that the total amount of energy required to obtain fuel-grade ethanol from the fermentation liquor is about 60% of the theoretical heating value of the ethanol product. This is a significant disadvantage for the large scale production of essentially water free ethanol for use as an ingredient in the production of gasoline - alcohol mixtures (commonly known as gasahol) which are to be used as motor fuels. If, in fact, ethanol is to find acceptable commercial utility as a motor fuel ingredient, the energy required to produce the substantially water free ethanol must be less than the energy required to recover substantially water free ethanol from fermentation liquors. Moreover, the conventional distillation and recovery process is complicated since it requires three distinct processing steps which are the (1) beer still, (2) the fractionator, and (3) the azeotropic distillation with benzene. A need, therefore, continues to exist for a method by which substantially water free alcohol, particularly ethanol, can be obtained using substantially less energy for the recovery of alcohol in comparison to conventional alcohol recovery procedures.

SUMMARY OF THE INVENTION

Accordingly, one object of the present invention is to provide a technique by which substantially water free alcohol can be produced under conditions which reduce energy consumption to about 20% or less of that required by conventional methods.

Another object of the present invention is to simplify recovery methodology for substantially water free alcohol from aqueous fermentation liquors.

Still another object of the present invention is to provide a method of recovering substantially water free alcohol from aqueous fermentation liquors which utilize the low grade heat generated by the fermentation process.

Briefly, these objects and other objects of the present invention as hereinafter will become more readily apparent can be attained by a method of producing alcohol substantially free of water by fermenting a fermentable biomass feedstock in a fermentation unit, thereby forming an aqueous fermentation liquor containing alcohol, extracting the aqueous fermentation liquor with an organic solvent containing an extractant for the alcohol, thereby forming an alcohol-solvent extract phase and an aqueous raffinate, contacting the alcohol-organic solvent phase with a carrier gas, thereby separating the alcohol from the alcohol-organic solvent phase, and separating alcohol substantially free of water from the carrier gas.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein:

the FIGURE is a flow diagram of an embodiment of the extraction-carrier gas stripping procedure of the present invention.

DETAILED DESCRIPTION OF THE PREFERRED EMBODIMENTS

The present invention involves a method of producing alcohol which is at least substantially free of water and preferably completely free of water. The term alcohol as used in the present invention embraces the common simple aliphatic alcohols, most particularly ethanol. Alcohol substantially free of water is known as fuel-grade alcohol, which is generally 96+% alcohol.

In order to obtain an aqueous alcohol solution suitable for processing by the technique of the present invention, a biomass feedstock is fermented in an aqueous medium by any conventional fermentation procedure utilized to prepare an aqueous fermentation liquor pregnant with alcohol. Standard fermentation conditions can be employed to prepare an aqueous fermentation liquor, and these procedures include continuous fermentation techniques.

Suitable biomass feedstocks which can be employed in the fermentation step of the present process include sugar based materials such as molasses, sugar cane, sugar beets and the like. Other biomass feedstocks include grains such as corn, wheat, barley, and the like.

The fermenting microorganisms which ferment the biomass feedstock can be any known microorganism used in fermentation processes to produce alcohols such as various species of yeast, thermophilic bacterium, and the like. Usually, fermentation is conducted at temperatures normally used in fermentation processes. However, when thermophilic bacteria are employed the temperature of fermentation can be very much higher. Thus, the fermentation temperature can range from 25° C. to 95° C.

After fermentation has continued to the point where a suitable aqueous fermentation liquor has been prepared, the fermentation liquor should be clarified by any known clarification procedure to remove suspended solids from the fermentation liquor. Once the aqueous liquor has been clarified, it is ready for further processing via the technique of the present invention.

As shown in the FIGURE, clarified fermentation liquors are passed into extraction unit 1 via line 3, where contact of the liquors with an organic solvent extractant system occurs. Extracted aqueous liquor is discharged from unit 1 as a raffinate by line 5. The organic solvent system enters unit 1 through line 7, and the solvent system pregnant with alcohol extracted from the aqueous liquor is discharged from unit 1 through line 9. Extraction of the aqueous liquor in unit 1 can be achieved by any conventional technique which is satisfactory for extracting the alcohol from the aqueous liquor at a temperature which is not critical, but usually ranges from 25° C. to 95° C. Conventional countercurrent solvent extraction columns are preferred for the extraction step. With the withdrawal of alcohol laden extract from unit 1, the extract is heated in heat exchanger unit 11 where the extract is warmed by heat liberated from the compression of the carrier gas. The extract generally is heated to a temperature within the range of 40°–110° C. The warmed extract is then passed into a stripping tower 13 through line 10, where the alcohol is stripped from the solvent phase in the extract by a carrier gas entering tower 13 through line 15, which has also been warmed in heat exchanger unit 17 from excess heat resulting from the carrier gas compression. The carrier gas is warmed to a temperature within the range of 40°–110° C. In the stripping unit 13, the preferred mode of contact of the extract with the carrier gas is counter-current stripping of the alcohol from the extract with the carrier gas. This stripping process removes alcohol from the solvent phase before the solvent phase is discharged from tower 13 through line 19. Pump 21 forces the solvent through line 23 into heat exchanger 25 where the solvent is cooled to a temperature sufficient for contact with aqueous fermentation liquor in extraction unit 1, which temperature generally ranges from 25° C. to 95° C. In the stripping process, a vapor of carrier gas and vaporized alcohol forms which enters the demisting and scrubbing section of tower 13, where a small fraction of fuel-grade alcohol is employed to scrub the carrier gas laden with alcohol. The stripping tower can contain a rectification unit which is used with or in place of the demisting section. The tower can also contain a scrubbing section. Fuel-grade alcohol discharged from the demister of unit 13 is conveyed to extraction unit 1 via line 45, where the alcohol is employed to dry the extract phase. In other words, the alcohol removes water from the organic solvent system. The scrubbing process, line 43, functions by further drying the carrier gas and reducing solvent losses to the alcohol product. The scrubbed carrier gas-alcohol mixture is then discharged from tower 13 through line 27 and compressed by compressor 29 through line 31 to cooler 33. The compressed gases are cooled in cooler 33, where some of the alcohol is condensed. The gases exiting cooler 33 through line 35 enter demister 37 or equivalent device, where the alcohol is recovered as a bottoms condensate. The carrier gas separated in unit 37 is then passed to heat exchanger unit 17 through line 39. Alternatively, if necessary, the alcohol laden carrier gas can be passed on to one or more additional condensation units for more extensive condensation and removal of alcohol from the carrier gas. In some cases, these additional condensation units will utilize some refrigeration whose heat may be pumped to supply either exchanger 11 or 17. The majority of the substantially dry alcohol from demister 37 is removed through line 41 as a product for use in whatever application desired. Smaller amounts of fuel-grade alcohol are withdrawn through line 43 for use in drying alcohol laden carrier gas in tower 13 and column 1. The above embodiment of the present process for preparing substantially dry alcohol represents only a preferred embodiment and should not be construed as the only method by which the objective of the present invention can be achieved.

The carrier gas which is used to strip alcohol from the extraction solvent should be one which is inert to the materials in the stripping tower and should be capable of stripping alcohol from the alcohol laden solvent in the stripping zone. Accordingly, suitable carrier gases include such relatively inert gases as air, ammonia and nitrogen, the inert gases such as helium, argon and the like, carbon dioxide and the like. The carrier gas should also contain some amount of a gas capable of drying the alcohol, and enhancing the ethanol stripping, which is removed in stripping unit 13. Suitable such drying/stripping gases include ammonia and the like. The amount of drying/stripping gas in the carrier gas is not critical and should be present in an amount sufficient to dry the alcohol stripped from stripping unit 13, if the level of drying from the extraction step is not sufficient. In fact, in some instances the drying/stripping gas may be used alone as the carrier gas without dilution by an inert carrier gas. A preferred embodiment of the carrier gas is one which contains 80 vol % $N_2$ and 20 vol % $NH_3$. As the ammonia interacts with water in the fluid mixture in stripping unit 13, ammonium hydroxide is formed which is dissolved in the solvent system and conveyed back to extraction unit 1 with the recycled solvent. Eventually, ammonium hydroxide is discharged from the system with the aqueous raffinate discharged from extraction unit 1. Also, the ammonia enhances ethanol stripping and improves the process efficiency.

In the alcohol-solvent separation unit 13 (the stripping tower) alcohol is separated from the components of the organic solvent, the relative ease of which separation is determined by the solvent of the solvent system chosen. Preferably, a high molecular weight solvent is selected so that the vapor pressure of the solvent is much less than the vapor pressure of the dissolved alcohol. The solvent contains an organic extractant component which is a compound which readily complexes with alcohol and at the same time is one in which water is essentially immiscible. Under these limitations, the relative volatility difference between the alcohol and solvent will be large, while the relative volatility difference between the alcohol and water will be substantially smaller, thus facilitating the separation process.

The ability of an organic extractant to efficiently separate two similar molecules such as water and an alcohol depends on a delicate balance between several structural features. Factors such as hydrogen bonding capabilities, charge distribution, steric environment of coordinating centers and hydrophobic-hydrophilic balance are important considerations in recovering fuel grade alcohol efficiently. In tests with tri-n-butylphosphate as an extractant in a hydrocarbon solvent with ethanol as the alcohol, the data obtained strongly suggest that a complex consisting of one molecule of tri-n-butylphosphate and one molecule of ethanol is formed and that accompanying this is the formation of a complex consisting of two molecules of tri-n-butylphosphate and approximately four water molecules. The mechanistic implications of these deductions suggest the basis for a strategy in selecting organic molecules which should enhance alcohol complexation and diminish the interaction of the extracting agent with water molecules. Clearly, the presence of a zwitter ionic structure in the extractant molecule (or semi-polar bond) in which negative charge in the molecule protrudes into the organic solvent medium and the positive charge is embedded in a hydrophobic environment are important structural features. This arrangement should heighten the hydrogen bonding capabilities of the extractant and diminish the extent of aggregation of extraction in the hydrocarbon solvent. In order to decrease the degree of water complexation structural features should be incorporated in the extractant that prevent the two extractant molecules from becoming proximate to one another to form a bridged structure with bridging water molecules. Secondary hydrogen bonding sites such as —O—R components should be either eliminated or sterically encumbered so as to prevent additional interactions with water molecules. Finally, enough hydrophobic hydrocarbon framework should be incorporated into the extractant molecules to prevent any significant solubility in the aqueous phase of the extraction zone. These considerations and restrictions suggest the following types of compound which include symmetric and unsymmetric alkyl and aryl phosphates, phosphonates, phosphine oxides, sulfoxides, sulfones, amine oxides and quaternary ammonium and phosphonium salts of sterically hindered carboxylic acids possessing structural features which facilitate alcohol complexation.

Suitable examples of organic extractant compounds for use in the organic solvent include mixed isomers of tridecanol, decanol, and 5,8 diethyl-6,7-dodecyl diol and other similar high boiling aliphatic and aromatic alcohols such as dodecyl phenol. Suitable extractant diluents include substances such as n-dodecane, kerosene, diisopropylbenzene and the like. A typical solvent will contain 30 to 60 volume % of the high-boiling alcohol in the diluent, but some applications could use as little as 5 vol % alcohol or as high as 90% alcohol in the diluent.

In the formulation of a suitable solvent for the extraction of alcohol from an aqueous alcohol solution, a hydrophobic solvent component which is completely miscible with the organic extractant molecule should be employed. Suitable hydrophobic liquids include aliphatic hydrocarbons such as dodecane, gasoline, kerosene and the like, and aromatic diluents such as diisopropylbenzene.

The scope of the organic solvent system also includes extractants which are capable of hydrogen bonding with water or alcohol. Suitable organic extractants capable of hydrogen bonding include alkyl and aromatic alcohols, carboxylic acids and ethers. Among the alcohols, the high boiling alcohols, i.e. those containing long carbon atom chains of about ten or more, are preferred. In fact, the high boiling alcohols as solvent systems within themselves can be used without a hydrophobic solvent component. Other alcohols include mixed isomers of isodecanol, 2-ethylhexanol, 2-methyl-2-pentanol, 4-heptanol, 3-ethyl-3-pentanol and the like, as well as diols and triols. The mixed isomers of tridecanol are especially preferred as an extractant.

The fuel-grade alcohol product obtained by the process of the present invention can be used for whatever purpose fuel-grade alcohol is used. A preferred utility of the fuel-grade alcohol, particularly fuel-grade ethanol, obtained by the present process is as a motor fuel additive.

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. A method of preparing alcohol, comprising:
   fermenting a fermentable biomass feedstock in a fermentation unit at a temperature of between about 25° C. and about 95° C., thereby forming an aqueous fermentation liquor containing alcohol;
   extracting said aqueous fermentation liquor with an organic hydrophobic solvent containing an extractant for said alcohol at a temperature of between about 25° C. and about 95° C., thereby forming an alcohol-organic solvent extract phase and an aqueous raffinate, said extractant being dissolved in said organic solvent and being selected from the group consisting of isodecanol, 2-ethylhexanol, 2-methyl-2-pentanol, 4-heptanol, 3-ethyl-3-pentanol, symmetrical and unsymmetrical alkyl phosphate, symmetrical and unsymmetrical aryl phosphate phosphonate, phosphine oxide, sulfoxide, sulfone, amine oxide, quaternary ammonium salt of a sterically hindered carboxylic acid; quaternary phosphonium salt of a sterically hindered carboxylic acid, ether, high boiling alcohol having an alkyl group of at least ten carbon atoms, and mixtures thereof;
   removing said alcohol-organic solvent extract phase from said aqueous raffinate;
   contacting said alcohol-organic solvent extract phase with a carrier gas thereby separating said alcohol from said alcohol solvent extract phase and forming an alcohol laden carrier gas vapor; and
   separating said alcohol from said carrier gas.

2. The method of claim 1, which further comprises:
   clarifying said aqueous fermentation liquor prior to extraction.

3. The method of claim 1, wherein said carrier gas is a mixture of nitrogen and ammonia.

4. The method of claim 1, which further comprises:
   scrubbing said vapor with fuel-grade alcohol to dry said vapor, and scrubbing said extract phase to dry said organic solvent.

5. The method of claim 1, which further comprises:
   recycling the solvent phase stripped of alcohol by said carrier gas to said extraction step.

6. The method of claim 1, which further comprises:
   recycling said carrier gas freed of alcohol to said step in which said alcohol-organic solvent is contacted with said carrier gas.

7. The method of claim 1, wherein said biomass feedstock is molasses, sugarcane or sugarbeets, or a grain selected from the group consisting of corn, barley and wheat.

8. The method of claim 1, wherein a hydrophobic solvent component forms a portion of said organic solvent, said solvent component being a hydrocarbon selected from the group consisting of dodecane, diisopropylbenzene, kerosene and gasoline.

9. The method of claim 1, wherein said solvent contains an extractant which is capable of hydrogen bonding with water or alcohol.

10. The method of claim 1, wherein said alcohol is removed from said alcohol-organic solvent extract phase by said carrier gas at a temperature of 40° C. to 110° C.

11. The method of claim 1, wherein the alcohol product of fermentation is ethanol.

* * * * *